United States Patent [19]

Schmieder et al.

[11] Patent Number: 4,543,417

[45] Date of Patent: Sep. 24, 1985

[54] ω,ω-DIACYLOXY-2,6-DIMETHYL-OCTA-TRIENOATES AND -OCTATRIENALS, THEIR PREPARATION AND THEIR USE FOR THE SYNTHESIS OF TERPENE COMPOUNDS

[75] Inventors: Klaus Schmieder, Frankenthal; Joachim Paust, Neuhofen; Rolf Fischer, Heidelberg; Hans-Martin Weitz, Bad Durkheim, all of Fed. Rep. of Germany

[73] Assignee: BASF Aktiengesellschaft, Fed. Rep. of Germany

[21] Appl. No.: 555,394

[22] Filed: Nov. 28, 1983

[30] Foreign Application Priority Data

Nov. 30, 1982 [DE] Fed. Rep. of Germany ..... 32442726

[51] Int. Cl.$^4$ .................. C07D 319/06; C07C 67/02
[52] U.S. Cl. ................... 549/375; 560/190; 560/205; 560/262
[58] Field of Search ............ 560/262, 190, 199, 205; 549/375

[56] References Cited

U.S. PATENT DOCUMENTS

| | | | |
|---|---|---|---|
| 3,236,879 | 2/1966 | Chuisoli | 560/190 |
| 3,634,518 | 1/1972 | Buddrus | 260/606.5 P |
| 3,989,758 | 11/1976 | Ruegg et al. | 260/602 |
| 4,284,796 | 8/1981 | Fischer et al. | 560/262 |
| 4,410,719 | 10/1983 | Fischer et al. | 560/262 |

FOREIGN PATENT DOCUMENTS 0900586 7/1962 United Kingdom .............. 560/262

OTHER PUBLICATIONS

Helv. Chim. Acta 69, 369, (1966).
J. Chem. Soc., 1965, 2019.
Chem. Ber. 107, 2050, (1974).
Org. Reactions, vol. 14, pp. 271–291, (1965).
Chem. Rev. 74, 87, (1974).

*Primary Examiner*—Ethel G. Love
*Attorney, Agent, or Firm*—Keil & Weinkauf

[57] ABSTRACT

ω,ω-Diacyloxy-2,6-dimethyl-octatrienoates and -octatrienals, as novel bifunctional asymmetric $C_{10}$ building blocks for terpene syntheses, which possess a formyl or alkoxycarbonyl group at one chain end and 2 geminal acyloxy groups at the other, and a process for their preparation from readily obtainable industrial $C_5$ building blocks and their use for the synthesis of terpene compounds by carbonyl olefination under conventional conditions.

6 Claims, No Drawings

ω,ω-DIACYLOXY-2,6-DIMETHYL-OCTATRIENO-ATES AND -OCTATRIENALS, THEIR PREPARATION AND THEIR USE FOR THE SYNTHESIS OF TERPENE COMPOUNDS

The present invention relates to novel bifunctional asymmetric $C_{10}$ building blocks for terpene syntheses, which have a formyl or alkoxycarbonyl group at one chain end and 2 geminal acyloxy groups at the other, and to a process for their preparation from readily available industrial $C_5$ building blocks, and to their use for the synthesis of terpene compounds by carbonyl olefination under conventional conditions.

Helv. Chim. Acta 49 (1966), 369 and U.S. Pat. No. 3,989,758 disclose $C_{10}$ building blocks of the type formed from compounds of the formula I by hydrolysis of the acylal function. Their use for the syntheses of β-apo-[′-carotenal and ethyl β-apo-8′-carotenate is also described in these publications. However, to date it has only been possible to prepare these $C_{10}$ building blocks by complicated multi-stage syntheses. For example, according to Helv. Chim. Acta (Loc. cit.), ethyl 2,6-dimethyl-8-oxoocta-2,4,6-trien-1-oate is prepared by a six-stage synthesis, with a total yield of less than 35%. According to Helv. Chim. Acta (loc. cit.) and J. Chem. Soc. 1965, 2019, the synthesis of 8,8-dimethoxy-3,7-dimethylocta-2,4,6-trien-1-al requires as many as 8 stages, and gives a yield of less than 10%.

It is an object of the present invention to propose, for the synthesis of β-apo-8′-carotenal and of ethyl β-apo-8′-carotenate and for other syntheses in terpene chemistry, $C_{10}$ building blocks which are just as suitable for this purpose as the $C_{10}$ aldehydes described in the prior literature stated but which can be synthesized more readily.

We have found, surprisingly, that this object is achieved by means of compounds of the formula I

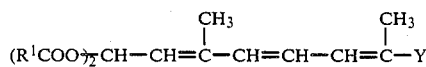

where Y is —COOR$^1$, formyl or an acetalated formyl group and R$^1$ is a low molecular weight alkyl radical.

In this formula, R$^1$ is preferably a straight-chain or branched alkyl radical of 1 to 5 carbon atoms or, where Y is an acetalated formyl group, is preferably a radical chain of the formula

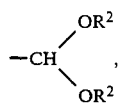

where R$^2$ is a straight-chain or branched alkyl radical of 1 to 5 carbon atoms or alkylene or alkenylene, each of 2 to 4 chain carbon atoms.

The novel compounds of the formula I are obtained, for example, if a compound of the formula II

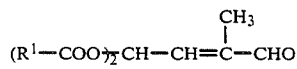

is reacted with a triarylphosphonium salt of the formula III

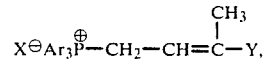

where X is chlorine or bromine and R$^1$ and Y have the above meanings, in the presence of an alkyl epoxide or under non-protic basic conditions. The Wittig reaction in the presence of an alkyl epoxide, in the form of the Buddrus variant, is known in the literature (cf. German Pat. No. 1,768,680 and Chem. Ber. 107 (1974), 2050); however, the use of this reaction in connection with the highly sensitive acylals has not been described to date. Regarding the reaction conditions, the stated publication is hereby incorporated by reference.

Specifically, the reaction is advantageously carried out as follows: equivalent amounts of compound II and of compound III are stirred with 1–10 equivalents of an alkyl epoxide at 0°–60° C. The solvent used is either excess alkyl epoxide, or any other solvent which is inert under the reaction conditions, eg. methylene chloride, dimethylformamide, methanol or tetrahydrofuran. The desired product can be separated from triphenylphosphine oxide, which is also formed, either by washing with aqueous dimethylformamide or aqueous methanol, or by crystallizing either the triphenylphosphine oxide or the desired product.

Alternatively, the compounds of the type I can be prepared by means of a Wittig reaction of II with III under non-protic basic conditions, (eg. in a conventional manner, using butyl-lithium/tetrahydrofuran; cf. A. Maercker, Org. Reactions, vol. 14, pages 271–490). In this case, a phosphonium salt of the type III is suspended, for example in tetrahydrofuran, and butyl-lithium and then an aldehyde II are added, the additions being carried out while cooling and under a protective gas atmosphere. When the reaction is complete, excess butyl-lithium is destroyed with methanol/water, and the reaction mixture is worked up in a conventional manner.

Another possible method of preparation comprises reacting a phosphonate IV of the formula

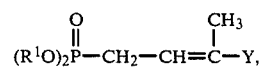

where R$^1$ and Y have the above meanings, with an acylal of the formula II, under the conditions of the Wittig-Horner reaction as described in Chem. Rev. 74 (1974), 87. The publication cited is hereby incorporated by reference, with regard to the reaction conditions stated therein.

Specifically, this reaction is carried out, for example, as follows: IV is converted to the phosphonate anion at from room temperature to 50° C. using sodium hydride in tetrahydrofuran, the carbonyl component II is then added dropwise and stirring is continued until the reaction is complete.

The resulting novel compounds of the formula I can be further processed either without isolation or after being isolated by extraction or crystallization; where Y is COOR$^1$ or

the conventional basic conditions of a Wittig reaction in a protic medium (eg. NaOEt/EtOH) ensure selective hydrolysis of the acylal function to the aldehyde, which then undergoes the actual Wittig reaction.

Compared to the acetal protective group conventionally used in terpene chemistry for aldehydes, the acyl function dispenses with a separate hydrolysis, since, in contrast to acetals, it can also be readily split off under basic conditions. On the other hand it permits the selective reaction of unprotected aldehyde functions in the molecule (eg. (I) Y=CHO) under non-protic conditions (eg. Wittig-Horner reaction, metal-alkyls in non-protic solvents) or under neutral conditions (Buddrus variant of the Wittig reaction).

The starting materials II and III or IV are obtainable from readily available precursors. For example, 2-methyl-4,4-diacyloxy-2-butenal is obtained in a simple manner by the process described in German Patent Application P No. 3125891.3, which is hereby incorporated by reference.

Components III and IV are obtained in a conventional manner from γ-chlorotiglaldehyde or γ-chlorotiglates, and the aldehyde group can be acetalated with, for example, neopentylglycol.

The bifunctional $C_{10}$ building blocks according to the invention are very useful for the synthesis of terpene compounds, for example of β-apo-8'-carotenates or β-apo-8'-carotenal, by reaction with a retinylphosphonium salt, for example according to the equation

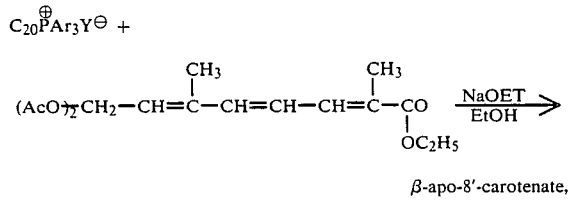

β-apo-8'-carotenate, very good yields being obtained.

In the same manner, β-apo-8'-carotenal is obtained by reacting a retinylphosphonium salt with the cyclic acetal of diacylaldimethyloctatrienal of the formula

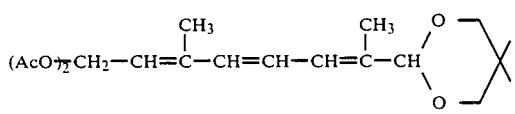

and hydrolyzing the acetal.

Compared with the process of U.S. Pat. No. 3,989,758, the use, according to the invention, of the novel intermediates has the advantage that these compounds are substantially easier to obtain and are no less suitable for the preparation of the end products.

Another possible use of the novel $C_{10}$ building blocks is for the preparation of β-carotene and retinal. If cyclogeranylphosphonium bromide is reacted with diacylaldimethyloctatrienal of the formula I (Y=CHO), the product is retinalacylal, which is converted to retinal using sodium ethylate in ethanol.

If retinalacylal is reacted further with a retinylphosphonium salt, β-carotene is obtained.

All these Wittig reactions are carried out under conventional conditions, as described in Org. Reactions, vol. 14, pages 271-490, which, regarding the details of the reaction, is hereby incorporated by reference.

EXAMPLE 1

Ethyl 2,6-dimethyl-8,8-diacetoxyocta-2,4,6-trienoate 1 mole of (3-ethoxy-carbonyl-3-methyl-2-propenyl)-triphenylphosphonium chloride and then, gradually, 1 mole of 2-methyl-4,4-diacetoxy-2-butenal were added to 500 g of butylene 1,2-oxide at 30° C., while stirring. The reaction mixture warmed up to about 60° C. during the dropwise addition of the butenal. Stirring was continued for 8 hours at 50° C., and the mixture was then allowed to cool to room temperature. The resulting solution contained, in addition to triphenylphosphine, 0.9 mole of the octatrienoate. The solution could be directly processed further to give the β-apocarotenate.

To obtain the crystalline product, 500 ml of methanol were added to the reaction mixture, which was then cooled to −10° C. and stirred for 6 hours at this temperature. Thereafter, the precipitated crystals were filtered off under suction and blown dry with nitrogen. 220 g of product (71%; purity 95%) were obtained; after recrystallization from ethyl acetate, the product melted at 106° C.

$^1$H-NMR: [δppm (multiplicity, integral)]: 1.33 (t, 3H), 2.02 (s, 3H), 2.04 (s, 3H), 2.11 (s, 6H), 4.25 (q, 2H), 5.67 (d, 1H), 6.57 (dd, 1H), 6.66 (d, 1H), 7.25 (d, 1H), 7.57 (d, 1H).

EXAMPLE 2

Ethyl 2,6-dimethyl-8,8-diacetoxyocta-2,4,6-trienoate 42.5 g (0.1 mole) of (3-ethoxycarbonyl-3-methyl-2-propenyl)-triphenylphosphonium chloride in 100 ml of dry dioxane were initially taken. First 47 g (0.11 mole) of n-butyl-lithium (15% strength in hexane) were added dropwise at 10° C., while stirring in an N₂ atmosphere; stirring was continued for 10 minutes, after which 20 g (0.1 mole) of 2-methyl-4,4-diacetoxy-2-butenal were added dropwise. Finally, the mixture was stirred for a further 8 hours while gradually warming up to room temperature.

To work up the mixture, 100 ml of hexane and 100 ml of a 6:4 mixture of methanol with H₂O were added, while cooling with ice. The phases were separated, and the hexane phase was washed with twice 100 ml of aqueous methanol (60%), dried with Na₂SO₄ and evaporated down in a rotary evaporator at 40° C. and under reduced pressure from a waterpump. The residue which remained consisted of 40.9 g of crystals, which according to NMR comprised 65% of ethyl 2,6-dimethyl-8,8-diacetoxyocta-2,4,6-trienoate and 35% of triphenylphosphine oxide. These crystals were stirred up in 50 ml of methanol at 0° C., the mixture was filtered and the filtrate was dried over Na₂SO₄; 20.5 g of the product were obtained in a purity of above 90%.

EXAMPLE 3

Ethyl 2,6-dimethyl-8,8-diacetoxyocta-2,4,6-trienoate 0.96 g (40 millimoles) of sodium hydride was added to 100 ml of dry tetrahydrofuran under nitrogen. 4.66 g (20 millimoles) of (3-ethoxycarbonyl-3-methyl-2-propenyl)-phosphonate and then 4.0 g (20 millimoles) of 2-methyl- 4,4-diacetoxy-2-butenal were added dropwise at 50° C., while stirring. Stirring was continued for 6 hours at 50° C., after which the mixture was allowed to cool to room temperature, 50 ml of H$_2$O were added dropwise, the phases were separated, the aqueous phase was extracted with three times 50 ml of diethyl ether, and the combined organic phases were finally extracted with twice 100 ml of saturated NaCl solution.

Drying (Na$_2$SO$_4$) and evaporating down the solution gave 5.71 g of a partially crystalline residue, which according to NMR contained about 65% of ethyl 2,6-dimethyl-8,8-diacetoxyocta-2,4,6-trienoate. 3.2 g of pure product were obtained by crystallization from ethyl acetate.

EXAMPLE 4

2,6-Dimethyl-8,8-diacetoxyocta-2,4,6-trienal neopentylacetal 46 g (0.1 mole) of 3-methyl-3-(5,5-dimethyl-1,3-dioxolan-2-yl)-2-propenyltriphenylphosphonium chloride were suspended in 100 g of butylene 1,2-oxide. 20 g (0.1 mole) of 2-methyl-4,4-diacetoxy-2-butenal were added dropwise at room temperature, while stirring. Stirring was continued for 30 hours at room temperature, after which monitoring by thin-layer chromatography (silica gel, mobile phase 1:1 diisopropyl ether/n-hexane mixture) showed that the reaction was complete. The triphenylphosphine oxide formed was separated off by filtering the mixture over a short silica gel column (100 g of silica gel, elution with Et$_2$O). Evaporating down the solution under reduced pressure gave 32 g of oily 2,6-dimethyl-8,8-diacetoxyocta-2,4,6-trienal neopentylacetal in the form of an isomer mixture containing about 80% of the all-E isomer. This isomer was isolated for spectroscopic purposes by preparative high-pressure liquid chromatography (150×10 Si5, mobile phase 10:1.5 cyclohexane/diethyl ether mixture, detection: UV=280 nm). A colorless oil was obtained.

$^1$H-NMR [δppm (multiplicity, integral)]: 0.76 (s, 3H), 1.24 (s, 3H), 1.88 (s, 3H), 1.99 (s, 3H), 2.08–2.09 (4s, 6H), 3.52 (4d, 2H), 3.68 (4d, 2H), 4.77 (s, 1H), 5.54 (d, 1H), 6.2–6.4 (m, 2H), 6.62 (d, 1H), 7.5 (d, 1H).

EXAMPLE 5

2,6-Dimethyl-8,8-diacetoxyocta-2,4,6-trienal 34.5 g (0.1 mole) of 3-formylbuten-2-yltriphenylphosphine (prepared as described in Belgian Pat. No. 656,433) and 20.0 g (0.1 mole) of 2-methyl-4,4-diacetoxy-2-butenal in 100 ml of methyl t-butyl ether were initially taken. The stirred mixture was heated at 60° C. for 5 hours, after which an educt was no longer detectable by thin-layer chromatography (6:4 n-hexane/ether mixture). When the reaction mixture had cooled to room temperature, it was cooled further to −20° C. and was stirred for 2 hours at this temperature; the crystals precipitated during this procedure were isolated and found to be pure triphenylphosphine oxide. The mother liquor was evaporated down in a rotary evaporator. 28.6 g of a pale yellow oil were obtained, which according to NMR spectroscopy contained 84.5% of the octatrienal in the form of an isomer mixture and 15.5% of triphenylphosphine oxide. The product obtained in this form can be used for further reactions without additional purification. For spectroscopic purposes, pure all-E-2,6-dimethyl-8,8-diacetoxyocta-2,4,6-trienal was isolated from the crude product by crystallization from a 1:2 mixture of n-hexane and diethyl ether, and was obtained in the form of white or slightly yellowish nacreous flakes of melting point 99.5° C.

$^1$H-NMR [δppm (multiplicity, integral)]: 1.91 (s, 3H), 2.06 (s, 3H) 2.10 (s, 6H), 5.76 (d, 1H), 6.67 (d, 1H), 6.82 (dd, 1H), 6.94 (d, 1H), 7.58 (D, 1H), 9.50 (s, 1H).

EXAMPLE 6

Ethyl β-apo-8'-carotenate 660 g (1.05 moles) of retinyltriphenylphosphonium bisulfate and 310 g (1 mole) of pure ethyl 2,6-dimethyl-8,8-diacetoxyocta-2,4,6-trienoate in 2,000 ml of ethanol were initially taken. 2,000 ml of 2N sodium ethylate in ethanol were then added dropwise, while cooling with water and stirring, at a rate such that the temperature of the reaction mixture did not exceed 30° C. Stirring was continued for 24 hours at 30° C., after which the mixture was worked up at 55°–60° C. by adding 2,000 ml of n-heptane and 2,700 ml of water, separating off the aqueous lower phase and washing the organic phase with three times 2,000 ml of aqueous methanol (60%). Thereafter, the organic phase was concentrated to 900 ml, with water being separated off, 560 ml of methanol and 300 ml of isopropanol were added and the mixture was cooled gradually to 0° C. It was stirred for 2 hours at 0° C., after which the product was filtered off, washed with twice 300 ml of ice-cold methanol and blown dry with nitrogen. Yield: 236.5 g; melting point: 137°–138° C. (no depression with an authentic sample); specific extinction: $E_1^1$=2550 (at 449 nm in cyclohexane).

The mother liquor contained a mixture of stereoisomeric β-apo-8'-carotenates, including 18% of the all-E isomer. By photochemical isomerization in the presence of rose bengal as a sensitizer, the proportion of all-E isomer can be increased to 74.5% by irradiation for 10 minutes. After crystallization at 0° C. as described above, a further 145.2 g of pure β-apo-8'-carotenate are obtained.

Melting point: 137°–138° C. (no depression with an authentic sample) Specific extinction: $E_1^1$=2562 (at 449 nm in cyclohexane)

EXAMPLE 7

Ethyl β-apo-8'-carotenate 600 g of a reaction mixture obtained as described in Example 1 and containing 0.5 mole of ethyl 2,6-dimethyl-8,8-diacetoxyocta-2,4,6-trienoate according to NMR, and 800 ml of ethanol and 330 g (0.525 mole) of retinyltriphenylphosphonium bisulfate, were initially taken. 1,250 ml of 2N sodium methylate in ethanol were added dropwise, while cooling with water, at a rate such that the temperature did not exceed 30° C. Stirring was continued for 30 hours at 30° C., after which the mixture was worked up at 55°–60° C., as described in Example 6. First batch of crystals: 98.3 g Batch of crystals obtained after isomerization: 59.5 g The two batches of crystals were combined, and recrystallized from 2,000 ml of a 4:1 mixture of ethanol and n-heptane.

Yield: 148.6 g (64.6%) Melting point: 136°–138° C. Specific extinction: 2548 (at 449 nm in cyclohexane).

EXAMPLE 8

Ethyl β-apo-8'-carotenate

A solution of 310 g (1 mole) of ethyl 2,6-dimethyl-8,8-diacetoxyocta-2,4,6-trienoate and 290 g (5 moles) of magnesium hydroxide were added to 1,000 ml of 1 molar retinyltriphenylphosphonium bisulfate solution (prepared as described in German Published Application DAS 2,729,974). The suspension was stirred for 20 hours at 40° C., after which the mixture was worked up by a procedure similar to that described in Example 1.

First batch of crystals: 224.6 g Melting point: 136°–137.5° C. Specific extinction: 2555 (at 449 nm in cyclohexane) Batch of crystals obtained after isomerization: 94.8 g Melting point: 136°–138° C. Specific extinction: 2550 (at 449 nm in cyclohexane)

EXAMPLE 9

β-Apo-8'-carotenal 200 ml of 2N sodium methylate in methanol and a solution of 35.2 g (0.1 mole) of 2,6-dimethyl-8,8-diacetoxyocta-2,4,6-trienal in 50 ml of methanol were simultaneously added dropwise to a stirred solution of 57 g (0.1 mole) of retinyl-triphenyl-phosphonium chloride in 300 ml of methanol at 0° C. When the dropwise addition was complete, stirring was continued for 2 hours at 0° C. and then for 2 hours at room temperature. Thereafter, 500 ml of n-heptane and 500 ml of H$_2$O were added at 40° C., and the phases were separated. The organic phase was then washed with twice 300 ml of 60% strength aqueous methanol and was finally treated with 100 ml of 3N H$_2$SO$_4$ at 40° C., while stirring. After 2 hours, the mixture was allowed to cool to room temperature, stirring was continued for a further 5 hours and the product was filtered off. The yield of crude product was 32.3 g. After recrystallization (dissolving in 65 ml of CHCl$_3$, adding 160 ml of ethanol/-heptane and cooling to 0° C.) 28.1 g of pure β-apo-8'-carotenal were obtained.

Melting point: 138°–140° C. Specific extinction: 2640 (at 457 nm in cyclohexane)

EXAMPLE 10

Retinal 47.9 g (0.1 mole) of cyclogeranyl-triphenyl-phosphonium bromide in 500 ml of dioxane (distilled over KOH) were initially taken. 64 g (0.15 mole) of butyllithium (15% in hexane) were added dropwise, in the course of 15 minutes, to the stirred mixture at 10° C. under an N$_2$ atmosphere, and the mixture was stirred for a further 2 hours at 10° C. Thereafter, 31.5 g (0.1 mole, 84.5% strength, cf. Example 5) of 2,6-dimethyl-8,8-diacetoxyocta-2,4,6-trienal, dissolved in 50 ml of dioxane, were added dropwise under the same conditions, and stirring was continued for a further 2 hours while heating the mixture to room temperature and then for a further 3 hours at 40° C. The mixture was then cooled to 10° C., and first 20 ml of a 1:1 dioxane/water mixture, then 200 ml of water and finally 200 ml of diisopropyl ether were added dropwise. The dioxane/water phase was separated off, and extracted with twice 200 ml of diisopropyl ether. The combined organic phases were dried over Na$_2$SO$_4$, filtered and evaporated down to 100 ml. A solution of 0.2 mole of sodium ethylate in 100 ml of methanol was then added dropwise while stirring at room temperature, and the mixture was stirred for a further 4 hours. 100 ml of n-heptane and 100 ml of water were then added, the phases were separated, the aqueous methanolic phase was extracted with twice 100 ml of n-heptane, and the combined organic phases were concentrated to 60 ml and the residue was crystallized at −20° C. The cryatals were filtered off under suction via a cooled frit, and were blown dry with N$_2$.

Yield: 20.5 g Melting point: 61.5°–62.5° C. Specific extinction: 1530 (at 381 nm in ethanol)

We claim:

1. A compound of the formula

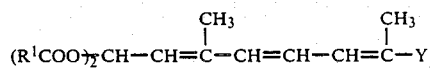

where Y is —COOR$^1$, formyl or an acetalated formyl group and R$^1$ is a low molecular weight alkyl radical.

2. A compound as claimed in claim 1, wherein Y is —COOR$^1$, —CHO or

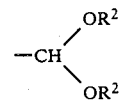

where R$^1$ and R$^2$ are each alkyl of 1 to 5 carbon atoms, and two R$^2$ radicals together can form an alkylene radical or an alkenylene radical of 2 to 4 chain carbon atoms.

3. A compound as claimed in claim 1, wherein Y is —COOC$_2$H$_5$ and R$^1$ is methyl.

4. A compound as claimed in claim 1, wherein Y is —CHO and R$^1$ is methyl.

5. A compound as claimed in claim 1, wherein Y is

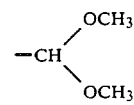

and R$^1$ is methyl.

6. A compound as claimed in claim 1, wherein Y is

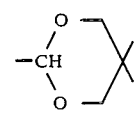

and R$^1$ is methyl.

* * * * *